United States Patent [19]

Bauer et al.

[11] 4,456,628

[45] Jun. 26, 1984

[54] PROCESS FOR FILM-COATING A PARTICULATE SOLID, AND EMULSIONS FOR CONDUCTING THE PROCESS

[76] Inventors: Kurt H. Bauer, Im Finkeler 4, D-7800 Freiburg 33; Hermann Osterwald, Blucherstr. 16, D-7800 Freiburg, both of Fed. Rep. of Germany

[21] Appl. No.: 223,157

[22] Filed: Jan. 7, 1981

[51] Int. Cl.³ .......................... A61K 9/30; A61K 9/36
[52] U.S. Cl. ......................................... 427/3; 106/170; 106/198; 424/35; 424/31; 427/2
[58] Field of Search .......................... 427/3, 2; 424/35; 106/170, 198

[56] References Cited

U.S. PATENT DOCUMENTS

| | | | |
|---|---|---|---|
| 2,722,528 | 11/1955 | Johnson | 106/198 |
| 2,843,583 | 7/1958 | Voris | 106/170 |
| 3,935,326 | 1/1976 | Groppenbacher et al. | 427/3 |
| 4,287,221 | 9/1981 | Tonedachi et al. | 427/3 |
| 4,385,078 | 5/1983 | Onda et al. | 427/3 |

FOREIGN PATENT DOCUMENTS

WO80/00659 4/1980 PCT Int'l Appl. .

*Primary Examiner*—Allan Lieberman
*Attorney, Agent, or Firm*—Hamilton, Brook, Smith & Reynolds

[57] ABSTRACT

A process of coating a particulate medicinal agent; comprising the application to said medicinal agent of a liquid composition containing a water-insoluble film-forming agent, a lipophilic solvent, a hydrophilic solvent and water, said liquid composition comprising an emulsion with at least two phases, wherein the liquid components of the liquid composition are removed after application of said liquid composition to said particulate medicinal agent.

4 Claims, No Drawings

PROCESS FOR FILM-COATING A PARTICULATE SOLID, AND EMULSIONS FOR CONDUCTING THE PROCESS

The invention relates to a process for the film-coating of a particulate solid, particularly a medicinal agent, as well as to an emulsion for conducting the process.

Providing a coating in the shape of a film, frequently also called "film-coating", is a relatively novel process, compared with the customary sugar-coating method.

According to the present state of the art, polymeric film-forming agents, especially those for gastric-juice-resistant or intestinal-juice-soluble encasing of solid medicinal preparations, e.g., cellulose acetate phthalate (CAP) and hydroxypropylmethylcellulose phthalate (HPMCP), are dissolved in suitable organic solvents, and these solutions are applied by means of suitable coating devices or machines to the solid medicinal preparations, for example granules, pellets, tablets, capsules, etc., for instance by spraying or pouring the solution over these preparations. The organic solvents are driven out or evaporated by hot air, radiant heat, or similar energy effects after the film-forming solution has been uniformly distributed over the solid, shaped medicine cores.

These conventional film-layering or film-coating processes exhibit the disadvantage that organic solvents must be employed, since the polymeric materials utilized for the coating of the solid medicinal preparations are water-insoluble. The use of organic solvents, however, is disadvantageous because of the toxicity of the solvents, their flammability, the costs, and harm to the environment. Chlorinated solvents are frequently employed as the organic solvents, and this, in particular, represents a great danger of pollution.

Since film-forming agents utilized for gastric-juice-resistant and intestinal-juice-soluble casings normally contain acidic groups in the molecule, so that they can be readily and quickly dissolved in the intestinal juice, which has a weakly alkaline reaction, attempts have also been made to introduce these film-forming agents in the form of their ammonium salts into aqueous application solutions. In this way, it was possible to obtain an aqueous solution and also to produce a casing around solid preparations.

The thus-obtained casings, however, did not show resistance to gastric juice in conformance with the requirements of the pharmacopoeia, since the ammonium salts are very stable, and the ammonia cannot be removed during the drying step, or at least cannot be eliminated quantitatively. The coatings produced according to this conventional process show a certain solubility and do not exhibit the gastric-juice-resistance required by the pharmacopoeia. Therefore, they are either dissolved during the gastric juice test, or they swell to such an extent that the gastric juice is capable of impairing the medicinal cores.

The present invention is based on the problem of providing coating processes for particulate medicinal agents wherein a minimum of polluting solvents is employed. According to the invention, media for conducting the process are likewise to be made available.

The invention concerns the incorporation of maximally large amounts of water into solutions consisting of polymeric water-insoluble film-forming agents dissolved in suitable organic solvents, without a coagulation or precipitation of the dissolved film-forming agents during this procedure. The incorporation of maximally large amounts of water into liquid preparations intended for encasing solid medicinal preparations has the purpose of dispensing as much as possible with polluting solvents. This purpose is difficult to achieve due to the strong tendency of the film-forming agents to precipitate in a tacky form even at the smallest amounts of water added to the organic solutions. However, a complete or partial precipitation is always connected with an impairment or even a loss of the film-forming properties.

It has now been found that, by formulating an emulsion, a considerable portion of the organic solvents can be replaced by water without an impairment of the film-forming characteristics of the film-forming agent by coagulation or swelling.

Accordingly, the invention relates to a process for the film-coating of a particulate, solid medicinal agent by coating the medicinal agent with a liquid containing a water-insoluble, polymeric film-forming agent, this process being characterized in that the medicinal agent is conventionally coated with a low-solvent emulsion containing at least two phases, one of which contains the dissolved film-forming agent and the major portion of a predominantly lipophilic solvent, and the other of which contains the major portion of a primarily hydrophilic solvent and water; and that the solvents are evaporated in a manner known per se.

Furthermore, the invention relates to an emulsion for conducting the process of this invention, which emulsion is characterized in that it contains a lipophilic solvent, a hydrophilic solvent, water, a water-insoluble, polymeric film-forming agent, and customary additives for film-coating, as well as optionally surface-active amphiphilic (containing hydrophilic and lipophilic moieties) materials.

The said emulsion is constructed on the basis of a solvent mixture which is distinguished by a specific ratio between hydrophilic and lipophilic solvents. Halogen-containing solvents are not utilized. The emulsion, in its final condition, consists of at least two phases, one of which contains the dissolved film-forming agent and the major portion of the predominantly lipophilic solvents, while the other contains the major portion of the primarily hydrophilic solvents and the water. If necessary, a third, for example solid, phase can be incorporated, for example consisting of color pigments or similar, solid adjuvants.

According to the invention, nonenteric and enteric coatings can be produced. However, gastric-juice-resistant coatings are preferably prepared according to the invention.

Preferred water-insoluble, polymeric film-forming agents are cellulose acetate phthalate (CAP), ethylcellulose, and hydroxypropylmethylcellulose phthalate (HPMCP).

The emulsions contain as the hydrophilic solvent preferably aliphatic alcohols of 1–5 carbon atoms, such as methanol, ethanol, propanol, or isopropanol, or the various isomeric butanols, lower aliphatic ketones of 1–6 carbon atoms, preferably acetone or methyl isopropyl ketone, mono- or diethers of ethylene glycol with aliphatic $C_1$–$C_5$ alcohols, such as ethylene glycol dimethyl ether, ethylene glycol monoethyl ether, or ethylene glycol monobutyl ether.

As the lipophilic solvent, the emulsions of this invention preferably contain $C_1$–$C_5$ alkyl esters of acetic acid, such as the methyl, ethyl, propyl, isopropyl, or butyl esters.

The emulsions of this invention can furthermore contain customary additives for film-coating, such as plasticizers, dyes, slip agents, or smoothing agents, etc. As for the details for conducting the film-coating process and the components thereof, please note the summary in "The Theory and Practice of Industrial Pharmacy", Second Edition, Lea & Febiger, Philadelphia 1976, Editors: Leon Lachman, Ph.D., Herbert A. Liebermann, Ph.D., and Joseph L. Kanig, Ph.D., pp. 368 et seq, the teachings of which are incorporated by reference.

The emulsions of this invention can contain emulsifier additives for stabilizing the emulsion. The quality of the emulsion can be improved by such additions. Examples for such emulsifiers are polyoxyethylene fatty acid esters, polyoxyethylene fatty alcohol ethers, glycerol mono- and di-fatty acid esters, sodium dioctyl sulfosuccinate, sodium lauryl sulfate, "Poloxalcol", and polyoxyethylene sorbitan fatty acid esters.

Further additives usable in film-coating are agents preventing or counteracting tackiness, wetting agents, or dispersants, flavoring agents, and sweeteners.

The composition of the emulsions according to this invention can vary greatly and depends on the special conditions of the materials to be coated. In general, the emulsions of this invention can contain 10–70% by weight, preferably 15–30% by weight, and most preferably 20–30% by weight of a lipophilic solvent; 5–40% by weight, preferably 10–20% by weight, and most preferably 15–20% by weight of a hydrophilic solvent; and 20–70% by weight, preferably 40–70% by weight, and most preferably 45–60% by weight of water, as the solvent system.

Normally, when producing the emulsions according to the invention, the organic film-forming agent and, if necessary, the surface-active amphiphilic material are dissolved in a mixture of lipophilic and hydrophilic solvents, whereafter the other components are optionally added, such as plasticizers, dyes, etc.; then, water is added to this mixture and the latter is dispersed with a homogenizer or with some other high-speed agitating device. The thus-obtained emulsion is subsequently utilized for the coating of the solid, particulate medicinal agents. The coating step takes place conventionally, in general so that the coated article absorbs 2–10% by weight, preferably 3–7% by weight of coating.

According to the invention, any types of particulate, solid materials can be coated, particularly medicinal agents, such as, for example, tablets, pills, capsules, pellets, grains, granules, or powders.

It is surprisingly possible to coat solid medicinal preparations by means of the emulsion of this invention qualitatively as well as quantitatively by using the customary mechanical installations just as satisfactorily as is presently done with the aid of the pure organic solutions of the film-forming agents. It is of significance from the viewpoint of recording technology that the thus-applied coatings do not differ with respect to their composition from those coatings applied from organic solvents.

The following advantages are attained according to the invention:

(1) The emulsion permits doubling of the concentration of film-forming agent without a rise in viscosity and without rendering application difficult or impossible.

(2) The emulsion does not require any chlorinated hydrocarbons, but rather only alcohols, esters and/or ethers which represent relatively little harm to the environment.

(3) As compared with the presently customary organic coating solutions, a total of about 75 solvents can be dispensed with and can be excluded from causing pollution, due to the increase in concentration and by the addition of water.

(4) As was found by corresponding experiments, the risk of ignition or explosion of the vapor mixtures driven off during the initial drying of the film coatings ranges far below the danger point.

The following examples will explain the invention.

EXAMPLE 1

Film-Coating with a CAP Dragee-Making Emulsion

A solution is prepared from 77 g CAP, 11 g of diethyl phthalate, and 25 g of a higher polyethylene glycol or glycerol polyethylene glycol ricinoleate and a mixture of 250 g of ethyl acetate, 80 g of a lower alcohol, and 90 g of an ether of ethylene glycol with lower alcohols.

This solution is combined with 450 g of water; then the mixture is dispersed with a magnetic stirrer and homogenized with a homogenizer (for example HO "Erweka"). This emulsion is subsequently applied in a dragee-making vessel by means of a compressed-air spray gun (two-component nozzle) to placebos until the weight increase amounts to 7% of the core weight. Colorless, glossy, and gastric-juice-resistant film-coated tablets are thus obtained.

EXAMPLE 2

Film-Coating with an HPMCP Dragee-Making Emulsion

A solution is prepared from 95 g HPMCP, as well as 40 g of an emulsifier of ethylene oxide and higher fatty alcohols or fatty acids and a mixture of 240 g of ethyl acetate, 65 g of acetone, and 105 g of ethylene glycol monoethyl ether. This solution is combined with 440 g of water, dispersed, and homogenized with the use of ultrasound. This emulsion is subsequently applied to dragee cores in a dragee-making vessel by coating with incremental portions or by the spraying method, until the cores show a 4% weight increase. In this way, glossy, colorless, and gastric-juice-resistant film-coated tablets are obtained.

EXAMPLE 3

Film-Coating with a Colored HPMCP Dragee-Making Emulsion

A dispersion is prepared from 436 g of water and 22 g of a mixture of titanium dioxide and a water-soluble or water-insoluble dye, using an "Ultra-Turrax" mixer; the product is then comminuted in a ball mill. This pigment suspension is added under agitation with a magnetic stirrer to a solution of 100 g HPMCP, 20 g of polyethylene glycol 400 stearate, "Tween 80", or other amphiphilic compounds in 240 g of ethyl acetate, 60 g of sec.-butanol, as well as 110 g of ethylene glycol monobutyl ether. After application to tablets up to a weight increase of at least 3%, glossy, colored, gastric-juice-resistant film-coated tablets are obtained which rapidly disintegrate in intestinal juice.

EXAMPLE 4

Film-Coating with an Ethylcellulose Coating Emulsion

Under heating, 23 g of ethylcellulose, 20 cp, and 6 g of polyethylene glycol 400 monostearate are dissolved in a mixture of 60 g of ethyl acetate, 16 g of a lower alcohol, e.g., isopropyl alcohol, and 25 g of an ethylene glycol ether, for example ethylene glycol monoethyl ether. A dispersion is prepared from this solution and 240 g of water. After application to tablets in a conventional method up to a weight increase of at least 3%, a smooth and glossy coating is obtained in the form of a film acting as a diffusion membrane.

EXAMPLE 5

Film-Coating with a Colored Ethylcellulose Dragee-Making Emulsion with the Addition of Hydroxypropylmethylcellulose A solution is prepared from 45 g of ethylcellulose, 10.5 g of polyethylene glycol (8) stearate, and 2.5 g of polyethylene glycol (100) stearate and a mixture of 140 g of ethyl acetate, 38 g of sec.-butanol, and 60 g of ethylene glycol monobutyl ether. Under agitation with a magnetic stirrer, this solution is combined with a dispersion of 3.0 g of titanium dioxide, 1.0 g of aluminum lacquer of a food dye in 450 g of water in which was furthermore dissolved 4.0 g of hydroxypropylmethylcellulose. After application to tablets in a conventional process up to a weight increase of at least 3%, glossy, colored film-coated tablets are obtained with a coating which can be considered to be a greatly swelling diffusion membrane in physiological fluids.

What is claimed is:

1. In the film-coating of a particulate medicinal agent including the steps of applying to said particulate medicinal agent a liquid composition containing a water-insoluble film-forming agent in a solvent therefor and thereafter drying off the liquid constituents of said liquid composition thereby to form a film on said particulate medicinal agent:

the improvement wherein said liquid composition is an emulsion including, by weight: (1) about 10–70% lipophilic solvent; (2) about 5–40% hydrophilic solvent; and (3) about 20–70% water; said emulsion comprising two phases, one of said phases containing the major portion of said lipophilic solvent with the water-insoluble film forming agent dissolved therein, and the other of the said phases containing the major portion of said hydrophilic solvent, the liquid components of the liquid composition being removed after application of said liquid composition to said particulate medicinal agent.

2. The improvement of claim 1 wherein said hydrophilic solvent is selected from $C_1$–$C_5$ aliphatic alcohols, $C_1$–$C_6$ aliphatic ketones, mono- or diethers of ethylene glycol with $C_1$–$C_5$ alcohols, or mixtures thereof.

3. The improvement of claims 1 or 2 wherein said lipophilic solvent comprises a $C_1$–$C_5$ alkyl ester of acetic acid or a mixture thereof.

4. The improvement of claim 3 wherein said water-insoluble film-forming agent is selected from cellulose acetate phthalate, ethylcellulose and hydroxypropylmethylcellulose phthalate.

* * * * *